(12) United States Patent
Hammoud et al.

(10) Patent No.: US 7,253,739 B2
(45) Date of Patent: *Aug. 7, 2007

(54) SYSTEM AND METHOD FOR DETERMINING EYE CLOSURE STATE

(75) Inventors: Riad I. Hammoud, Kokomo, IN (US); Phillip V. Malawey, Kokomo, IN (US)

(73) Assignee: Delphi Technologies, Inc., Troy, MI (US)

( * ) Notice: Subject to any disclaimer, the term of this patent is extended or adjusted under 35 U.S.C. 154(b) by 175 days.

This patent is subject to a terminal disclaimer.

(21) Appl. No.: 11/077,042

(22) Filed: Mar. 10, 2005

(65) Prior Publication Data

US 2006/0204042 A1   Sep. 14, 2006

(51) Int. Cl.
*G08B 23/00* (2006.01)

(52) U.S. Cl. .................. 340/575; 340/576; 340/573.1; 382/103; 382/104; 382/107; 382/117; 348/77; 348/78

(58) Field of Classification Search ................. 340/575, 340/576, 573.1; 382/107, 117, 278, 296, 382/103, 104; 348/77, 78
See application file for complete search history.

(56) References Cited

U.S. PATENT DOCUMENTS

| | | |
|---|---|---|
| 5,805,720 A | 9/1998 | Suenaga et al. |
| 6,243,015 B1 | 6/2001 | Yeo .............................. 340/576 |
| 6,571,002 B1 | 5/2003 | Ogawa ........................ 382/117 |
| 6,717,518 B1 | 4/2004 | Pirim et al. |
| 6,927,694 B1 * | 8/2005 | Smith et al. ................. 340/576 |
| 6,928,694 B2 | 8/2005 | Breed et al. |
| 7,043,056 B2 | 5/2006 | Edwards et al. |
| 2003/0169907 A1 | 9/2003 | Edwards et al. ............. 382/118 |
| 2004/0044293 A1 | 3/2004 | Burton ........................ 600/544 |

FOREIGN PATENT DOCUMENTS

| | | |
|---|---|---|
| EP | 1378861 | 1/2004 |
| JP | 2004/220080 | 8/2004 |
| WO | 2004/034905 | 4/2004 |

OTHER PUBLICATIONS

"A Drowsy Driver Detection System for Heavy Vehicles" by Richard Grace et al., 0-7803-5086-3/98 © 1998 IEEE, pp. I36-1 through I36-8.

(Continued)

*Primary Examiner*—Tai Nguyen
(74) *Attorney, Agent, or Firm*—Jimmy L. Funke (57) ABSTRACT

A system and method are provided for monitoring an eye to determine eye closure. The system includes a video imaging camera oriented to generate images of an eye. The system also includes a video processor for processing the images generated with the video imaging camera. The processor includes an edge detector for detecting edges of the eye in the image and a line selector for generating substantially horizontal first and second lines representative of the detected edges. The processor determines the state of eye closure, such as eye open or eye closed, based on distance between the first and second lines. The system may be employed on a vehicle to determine the eye closure of a driver of the vehicle.

19 Claims, 9 Drawing Sheets

OTHER PUBLICATIONS

"Drowsy Driver Monitor and Warning System" by Richard Grace, International Driving Symposium on Human Factors in Driver Assessment, Training and Vehicle Design, Aug. 2001, 7 pages.
"Research On Vehicle-Based Driver Status/Performance Monitoring: Development, Validation, And Refinement Of Algorithms For Detection Of Driver Drowsiness," U.S. Department of Transportation, National Highway Traffic Safety Administration, Dec. 1994.
EP Search Report Dated Jul. 10, 2006.
Libor Masek: "Recognition of Human Iris Patterns for Biometric Identification" 2003, XP002386033 Retrieved from the Internet: URL:http://144.122.166.80/reading/texts/iris_recog/LiborMasekThesis.pdf> *p. 7, paragraph 2-paragraph 4* *Figure 2.2.
M. Tistarello; E. Grosso: "Active vision-based face authentication" Image and Vision Computing, 2000, pp. 299-314, XP002390392 *abstract; figure 5* *p. 302, right-hand column.

* cited by examiner

SYSTEM AND METHOD FOR DETERMINING EYE CLOSURE STATE

CROSS-REFERENCE TO RELATED APPLICATIONS

This application is one of three applications filed on the same date, all commonly assigned, the other applications being identified as U.S. application Ser. No. 11/077,041, entitled "SYSTEM AND METHOD OF DETECTING EYE CLOSURE BASED ON EDGE LINES," and U.S. patent application Ser. No. 11/076,600, entitled "SYSTEM AND METHOD OF DETECTING EYE CLOSURE BASED ON LINE ANGLES," the entire disclosures of which are hereby incorporated herein by reference.

TECHNICAL FIELD

The present invention generally relates to eye monitoring and, more particularly, relates to monitoring an eye, such as one or both eyes of a driver of a vehicle, to determine whether the eye is open or closed.

BACKGROUND OF THE INVENTION

Video imaging systems have been proposed for use in vehicles to monitor a subject person such as the driver and other passengers in the vehicle. Some proposed video imaging systems include one or two cameras focused on the driver of the vehicle to capture images of the driver's face. The video images are processed generally using computer vision and pattern recognition techniques to determine various facial characteristics of the driver including position, orientation, and movement of the driver's eyes, face, and head. Some advanced eye monitoring systems process the captured images to determine eye closure, such as open, half-open (half-closed), and closed states of the eye(s).

By knowing the driver's facial characteristics, vehicle control systems can provide enhanced vehicle functions. For example, a vehicle control system can monitor one or both eyes of the subject driver and determine a condition in which the driver appears to be fatigued or drowsy based on simple statistical analysis of the cumulated results of open or closed state of the eye(s) over time. Standard human factor measures such as PerClos (percentage of eye closure) and AveClos (average of eye closure) could be used to determine the drowsiness state of the driver. For instance, if the AveClos value is determined to be above a certain threshold, the system may initiate countermeasure action(s) to alert the driver of the driver drowsy condition and/or attempt to awaken the driver.

Some proposed vision-based imaging systems that monitor the eye(s) of the driver of a vehicle require infrared (IR) illumination along with visible light filters to control scene brightness levels inside of the vehicle cockpit. One such driver monitoring system produces bright and dark eye conditions that are captured as video images which are processed to determine whether the eye is in the open position or closed position. Such prior known driver eye monitoring systems require specific setup of infrared illuminators on and off the optical camera axis. In addition, these systems are generally expensive, their setup in a vehicle is not practical, and they may be ineffective when used in variable lighting conditions, especially in bright sunny conditions. Further, variations in eyelash contrast and eye iris darkness levels for different subject persons may cause such prior systems to make erroneous eye state discrimination decisions.

It is therefore desirable to provide for a cost affordable and effective method for monitoring an eye and determining the eye closure state. In particular, it is desirable to provide for an eye monitoring system for discerning the open and closed states of the eye(s) of a driver of a vehicle that overcomes drawbacks of prior known proposed eye monitoring approaches.

SUMMARY OF THE INVENTION

In accordance with the teachings of the present invention, a system and method are provided for monitoring an eye and determining eye closure. According to one aspect of the present invention, the system includes a video imaging camera oriented to generate images of an eye. The system further includes a processor for processing the images generated with the video camera. The processor includes an edge detector for detecting edges of the eye in the image and a line selector for generating at least first and second lines representative of the detected edges. The processor determines a state of eye closure based on distance between the first and second lines.

According to another aspect of the present invention, the method includes the steps of arranging a video imaging camera to generate images of an eye and generating an image of the eye. The method also includes the steps of processing the image to identify edges of the eye in the image and generating at least first and second lines representative of the edges. The method further includes the step of determining an eye closure state based on distance between the first and second lines.

Accordingly, the system and method according to the present invention effectively determines the closure state of the eye, such as an open eye state or closed eye state, with a cost affordable and real-time eye monitoring system. The eye monitoring system is particularly useful in a vehicle for monitoring the eye(s) of a driver of the vehicle and determining if the driver's eye(s) are substantially closed (i.e., closed or almost closed).

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENT

Figure 1:
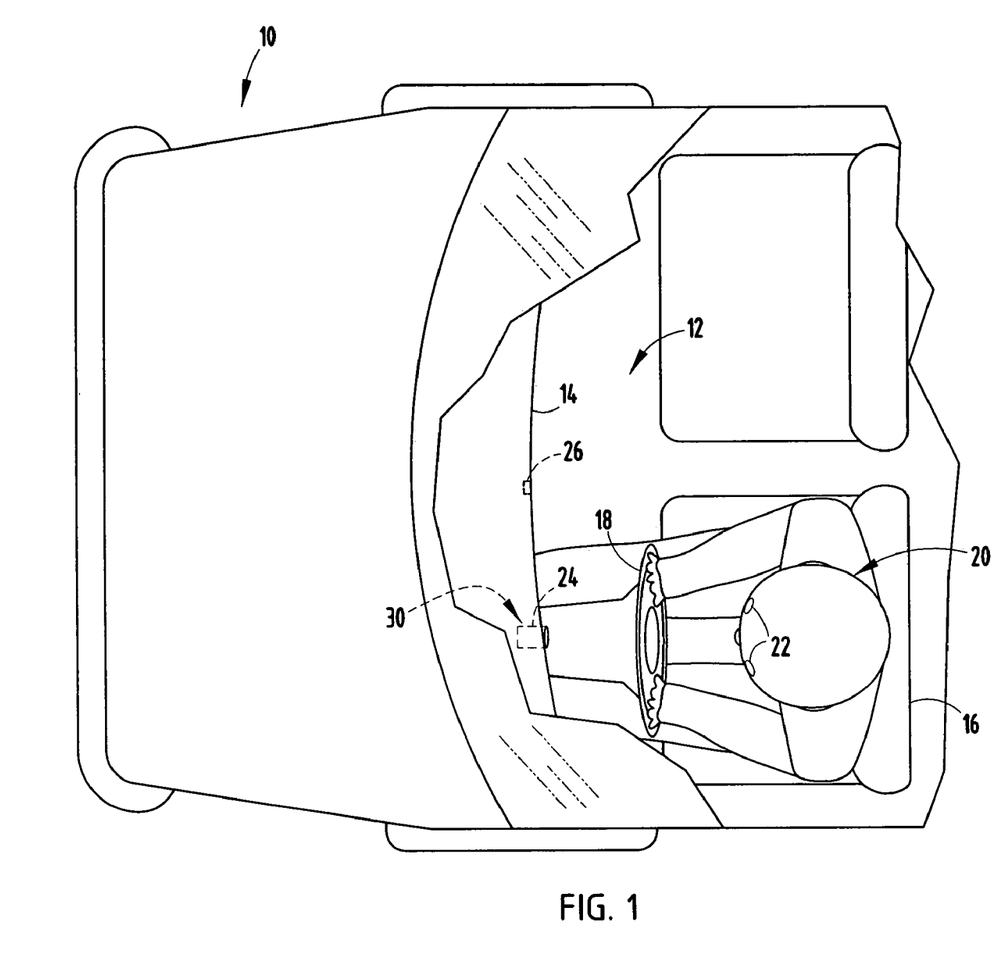
FIG. 1 is a top view of the cockpit of a vehicle equipped with an eye monitoring system for monitoring the eye(s) of a driver.

Referring now to FIG. 1, the passenger compartment (cockpit) 12 of a vehicle 10 is generally shown equipped with a driver eye monitoring system 30. The eye monitoring system 30 has a video imaging camera 24 oriented and focused on a subject person (driver) 20 driving the vehicle 10 for capturing and generating video images of the driver 20. The eye monitoring system 30 monitors one or both eyes of the person 20 and determines binary eye closure, e.g., open eye state or closed eye state.

The video imaging camera 24 is shown located generally in front of the driver's seat 16 in the front region of the vehicle cockpit 12. According to one embodiment, video imaging camera 24 is mounted in the instrument cluster. However, the camera 24 may be mounted in other locations onboard the vehicle 10 which allow for acquisition of video images capturing one or both eyes of the driver 20 of the vehicle 10. For example, the video imaging camera 20 may be mounted in the steering assembly 18 or mounted in the dash 14. While a single video imaging camera 24 is shown and described herein, it should be appreciated that two or more video imaging cameras may be employed in the eye monitoring system 30, without departing from the teachings of the present invention.

The video imaging camera 24 is arranged so as to capture successive video image frames of the region where the face of the driver 20 of the vehicle 10 is expected to be located during normal vehicle driving. More particularly, the acquired video image captures the driver's face including one or both eyes 22 and the surrounding ocular features generally found in the area referred to as the ocular adnexa. These features may include one or both eyes 22 and the pupil of the eyes 22, the upper (superior) and lower (inferior) eyelids, and the palpebral fissure space between the eyelids. The acquired video images are then processed to determine characteristics of one or both eyes 22 of the subject person (driver) 20. Each video frame image is processed to determine the eye closure state of one or both eyes 22 of the driver 20, such as open eye position or closed eye position states. By knowing the eye closure state, the eye monitoring system 30 allows for determination of a driver drowsiness condition or inattentive driver condition, among other uses.

The eye monitoring system 20 is also shown employing an optional light illuminator 26 located forward of the driver 20, such as in the dash 14, for illuminating the face of the driver 20. The light illuminator 26 may include one or more infrared (IR) light emitting diodes (LEDs). Either on-axis of off-axis LEDs may be employed (e.g., no specific IR setup is required, in particular). The light illuminator 26 may be located anywhere onboard the vehicle 10 sufficient to supply any necessary light illumination to enable the camera 24 to acquire video images of the driver's eye(s) 22.

Figure 2:
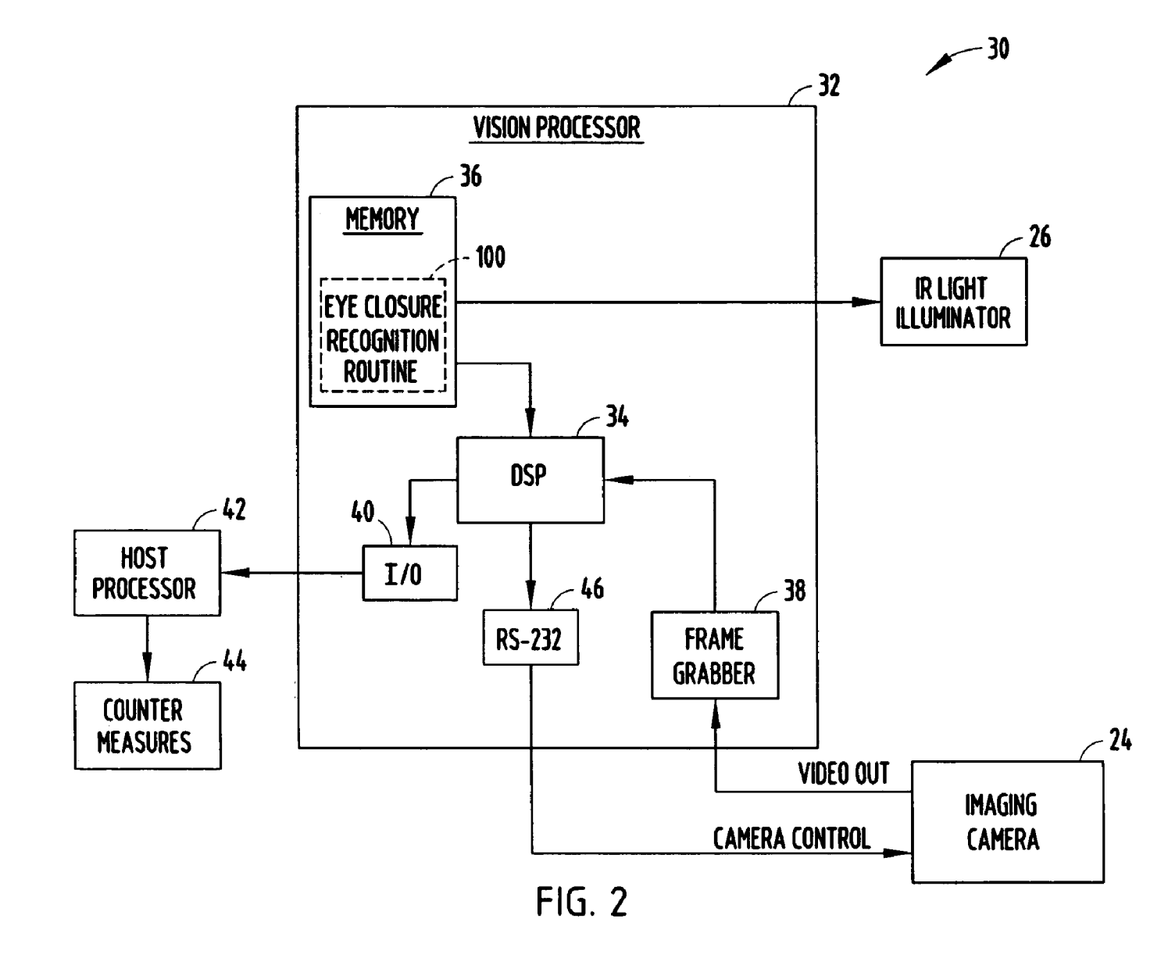
FIG. 2 is a block diagram illustrating the eye monitoring system according to the present invention.

Referring to FIG. 2, the eye monitoring system 30 is shown having the video imaging camera 24 and IR light illuminator 26 coupled to a vision processor 32 which, in turn, is coupled to a host processor 42. The video imaging camera 24 may include a CCD/CMOS active-pixel digital image sensor mounted as a chip onto a circuit board. One example of a CMOS active-pixel digital image sensor is Model No. PB-0330, commercially available from Photobit, which has a resolution of 640H×480 V. It should be appreciated that other imaging cameras may be employed.

The vision (video) processor 32 is shown having a frame grabber 38 for receiving the video output frames generated by the video imaging camera 24. Vision processor 32 also includes a digital signal processor (DSP) 34 for processing the acquired video image frames. The digital signal processor 32 may be a floating point or fixed point processor. The vision processor 32 further includes memory 36, such as random access memory (RAM), read-only memory (ROM), and other memory, as should be readily apparent to those skilled in the art. The vision processor 32 is configured to perform one or more routines for controlling activation of the IR light illuminator 26, controlling the video imaging camera 24, processing the acquired video images to determine eye closure state, and applying the processed information to vehicle control systems, such as host processor 42.

The vision processor 32 may provide camera control functions via control RS-232 logic 46 which allows for control of the video imaging camera 24 via camera control signals. Control of the video imaging camera 24 may include automatic adjustment of the pointing orientation of the video imaging camera 24. For example, the video imaging camera 24 may be repositioned to focus on an identifiable feature, and may scan a region in search of an identifiable feature, including the driver's face and, more particularly, one or both eyes 22. Camera control may also include adjustment of focus and magnification as may be necessary to track an identifiable feature. Thus, the eye monitoring system 30 may automatically locate and track one or more identifiable features, such as one or both of the driver's eyes 22.

The eye monitoring system 30 includes an eye closure recognition routine 100 stored in memory 36 and processed by the digital signal processor 34. Routine 100 may be implemented as a software program as should be evident to those in the art. The eye closure recognition routine 100 processes the captured video images of the eye 22 to determine the eye closure state (e.g., eye open position or eye closed position states).

Figure 3:
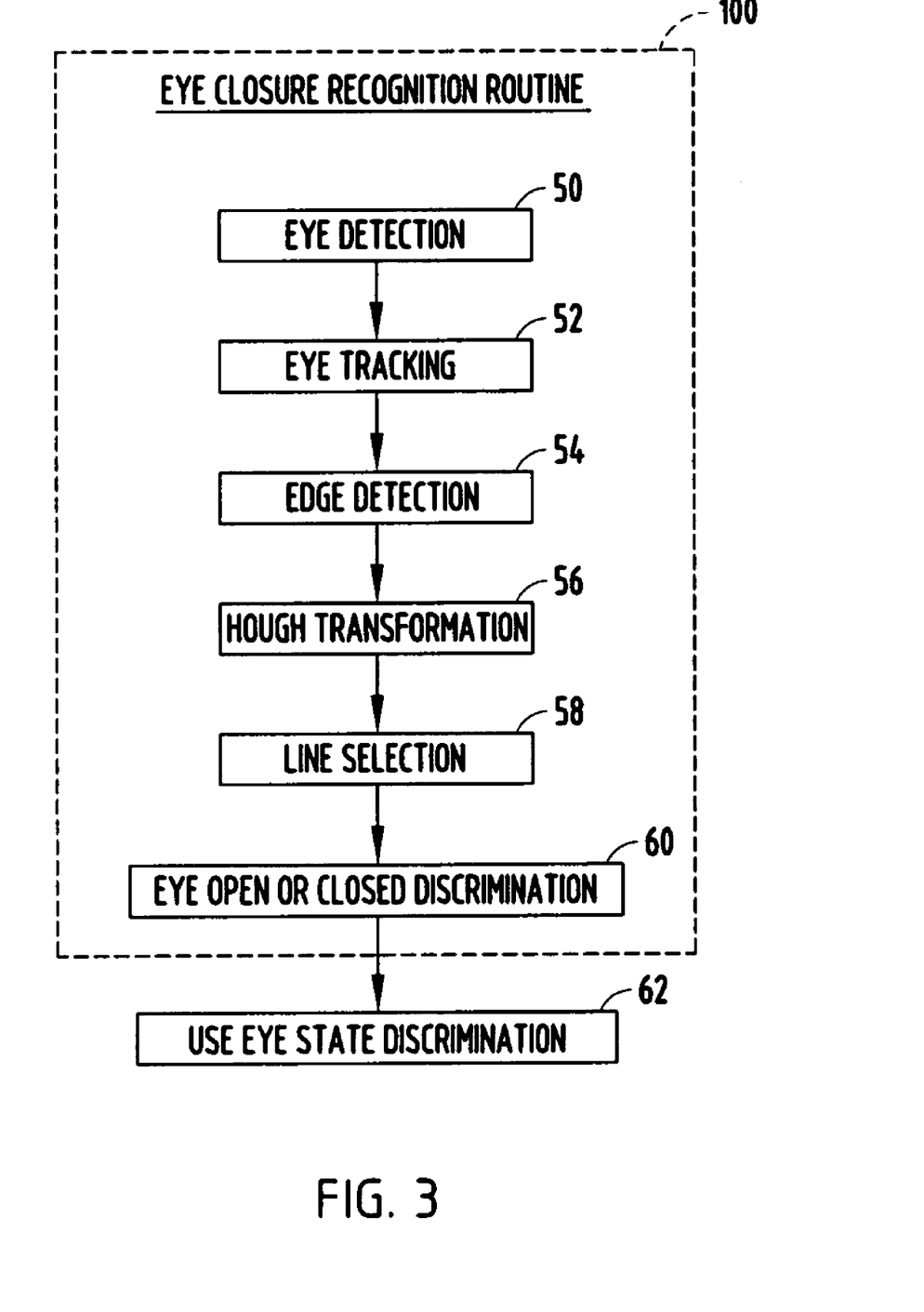
FIG. 3 is a block diagram illustrating functions performed by the eye closure recognition routine.

Referring to FIG. 3, the eye closure recognition routine 100 performs various functions including eye detection function 50 which detects one or both eyes, and eye tracking function 52 which tracks one or both detected eyes in the captured video images. Routine 100 also includes an edge detection function 54 for detecting edge boundaries of the eye in the captured image. Routine 100 performs a Hough Transformation function 56 to transform plotted edge pixel points from Cartesian coordinates to polar coordinates (space) to enable the generation of lines on the edge boundaries of the monitored eye 22. Routine 100 further includes a line selection function 58 for selecting a pair of lines that represent the upper and lower edge boundaries of the eye 22.

Routine 100 performs an eye open or closed discrimination function 64. The eye open or closed discrimination function 64 determines the state of eye closure. The eye closure determination is achieved by monitoring the edge boundaries of the monitored eye 22 and determining when the selected upper and lower lines are sufficiently close together such that the eye is substantially closed. The determined eye closure state may be employed in any of a number of applications in function block 62.

Referring back to FIG. 2, the determined eye closure state is made available to the host processor 42 via input/output (I/O) 40. The host processor 42 may include any of a number of control devices that may employ the determined eye closure state for use in any of a number of applications. For example, the determined eye closure state may be used in a driver drowsy application or other application(s) to initiate countermeasures 44. Examples of countermeasures 44 may include activating an audible warning, initiating a haptic seat, increasing vehicle following distance, initiating cold air conditioning (A/C), and/or activating peppermint olfactory stimulation.

Figure 4A:
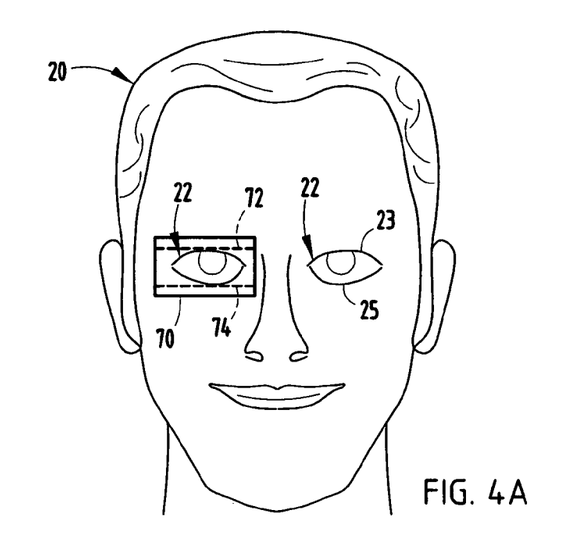
FIG. 4A is a pictorial representation of a video image captured by the camera showing open eyes of the driver.
Figure 4B:
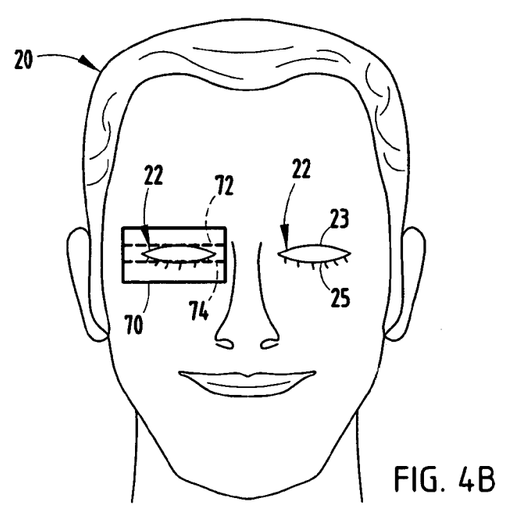
FIG. 4B is a pictorial representation of a video image captured by the camera showing closed eyes of the driver.

Referring to FIGS. 4A and 4B, representative video images generated with video imaging camera 24 capturing the driver's face 20 are shown, according to one example. One video image frame showing the eyes 22 in the open state is shown in FIG. 4A. Another video image frame showing the eyes 22 in the closed state is shown in FIG. 4B.

The eye closure recognition routine 100 detects an eye 22 and tracks a region shown bounded by an eye tracking window 70 generally centered about the eye 22. The eye tracking window 70 may include a rectangular sub-image having a size of 88×40 pixels, according to one example. The eye tracking window 70 may be of any shape and is of sufficient size to capture a region greater than the upper and lower edge boundaries of the monitored eye 22.

The monitored eye 22 is shown within eye tracking window 70 bounded by an upper horizontal line 72 and a lower horizontal line 74. The horizontal lines are oriented at angle $\phi=180°$ (or $0°$). Angle $\theta$ is equal to angle $\theta-90°$. The eye 22 has an upper eyelid 23 generally defining the upper edge boundary of eye 22 and a lower eyelid 25 generally defining the lower edge boundary of eye 22. With the monitored eye 22 in the open position as seen in FIG. 4A, the upper and lower horizontal lines 72 and 74, respectively, are separated by a greater distance as compared to when the eye 22 is in the closed position as seen in FIG. 4B. The eye closure recognition routine 100 generates and selects upper and lower substantially horizontal lines 72 and 74 and further determines the eye closure state based on the distance between lines 72 and 74. The distance between lines 72 and 74 may be computed by subtracting the number of pixels in the vertical (Y-axis) separating the two lines.

Figure 5A:
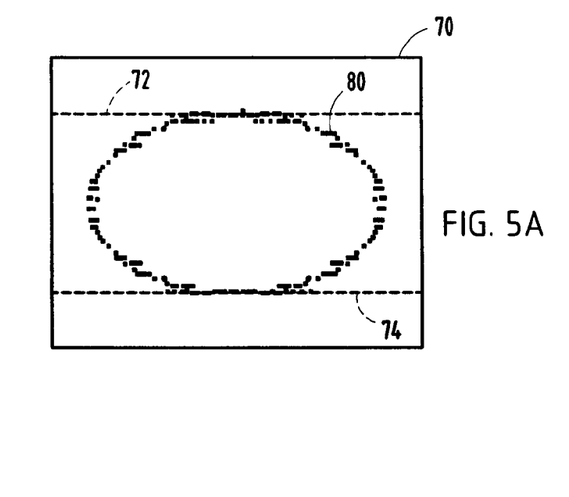
FIG. 5A is a gray-scale exploded view of the edge boundaries of the eye as captured in the image of FIG. 4A.
Figure 5B:
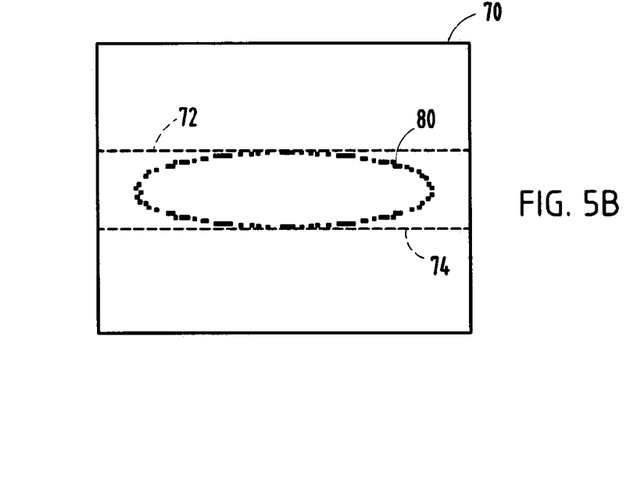
FIG. 5B is a gray-scale exploded view of edge boundaries of the eye as captured in the image of FIG. 4B.

The eye closure recognition routine 100 generates a gray-scale video image within window 70, detects the boundary edges 80 of the eye 22, generates substantially horizontal lines at $\theta=0°$ or $180°$, which is $\theta=90°$, and selects the uppermost and lowermost lines 72 and 74. The edge boundaries 80 of the eye 22 are shown in FIGS. 5A and 5B as a gray-scale image in which the pixels at the edge boundaries 80 exhibit a characteristic shading (e.g., dark gray contrasted with white, or vice versa) that identifies the edge boundaries 80 of the eye 22. The edge map (set of edge pixels) is computed using a standard edge detector. The eye closure recognition routine 100 plots the pixels exhibiting the characteristic gray-scale edge boundaries 80 in Cartesian coordinates and transforms the Cartesian coordinates to a polar space via a Hough Transformation.

From the Hough Transformation, lines that are substantially horizontal are extracted and, from the substantially horizontal lines, the upper and lower horizontal lines 72 and 74 are selected according to one embodiment. In this embodiment, the uppermost line at the boundary of the upper eyelid 23 and the lowermost line at the boundary of the lower eyelid 25 are selected. Alternately, lines 72 and 74 may be selected by choosing the most dense (strongest) line identifying the boundary of the upper eyelid 23 and the most dense (strongest) line defining the edge boundary of the lower eyelid 25 of the eye 22.

Figure 6A:
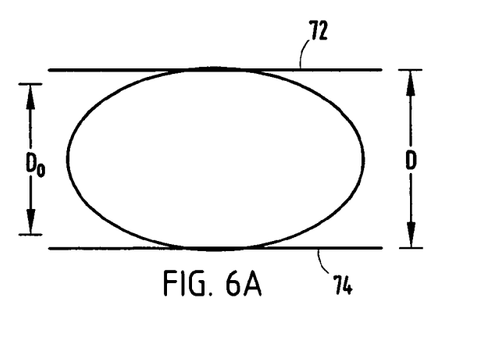
FIG. 6A is a schematic diagram illustrating line selection and eye closure recognition for an open eye state.
Figure 6B:
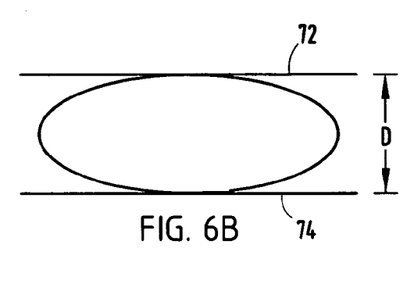
FIG. 6B is a schematic diagram illustrating line selection and eye closure recognition for a half-open (half-closed) eye state.
Figure 6C:
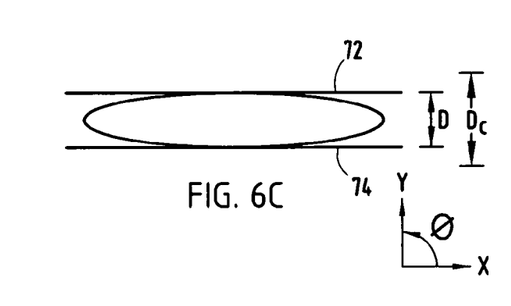
FIG. 6C is a schematic diagram illustrating line selection and eye closure recognition for a closed eye state.

Referring to FIGS. 6A-6C, the upper and lower substantially horizontal lines 72 and 74 are shown separated by a distance D that is indicative of the closure state of the monitored eye 22. As seen in FIG. 6A, the eye 22 is determined to be in an open state when the distance D between the upper and lower substantially horizontal lines 72 and 74 exceeds the open eye threshold $D_O$. When the distance D between the upper and lower substantially horizontal lines 72 and 74 is less than a closed eye threshold Dc, the eye 22 is determined to be in the closed position as seen in FIG. 6C. Otherwise, when the determined distance D between the upper and lower substantially horizontal lines 72 and 74 is between the open eye threshold $D_O$ and closed eye threshold $D_C$, the eye 22 is determined to be in the half-open state as shown in FIG. 6B.

The use of the Hough Transformation to generate substantially horizontal lines and select the upper and lower lines 72 and 74 is illustrated in FIGS. 7A-7D. The Hough Transformation transforms two-dimensional images with lines into a domain of possible linear parameters, where each line in the image provides a peak position at the corresponding line parameters. In the Hough Transformation, the angle $\theta=90°-\phi$. The Hough Transformation is generally known in the art of image processing and computer vision for detecting shapes and, in particular, straight lines. While a Hough Transformation is described herein in connection with the present invention, it should be appreciated that other transformations such as a Radon Transformation, or Least-square type methods for line fitting may be employed to generate substantially horizontal lines and select the upper and lower lines 72 and 74.

Figure 7A:
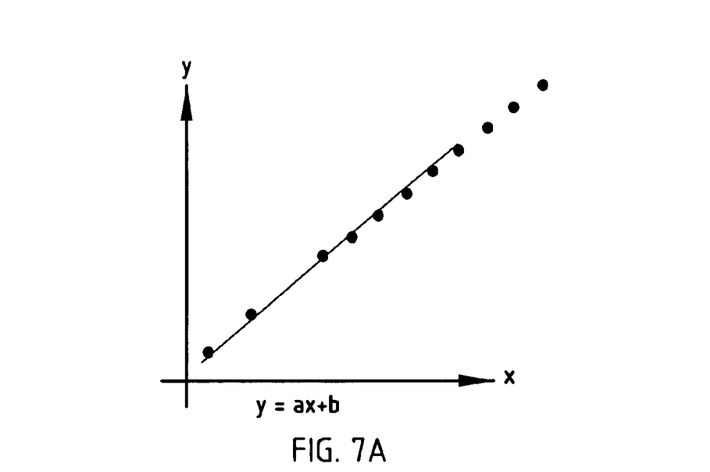
FIGS. 7A-7D illustrate the standard Hough Transformation for straight line detection, illustrating edge pixels plotted in Cartesian coordinates in FIG. 7A, transformed to (a, b) space in FIG. 7B, transformed to polar space in FIG. 7C, and lines mapped in a lookup table in FIG. 7D.
Figure 7B:
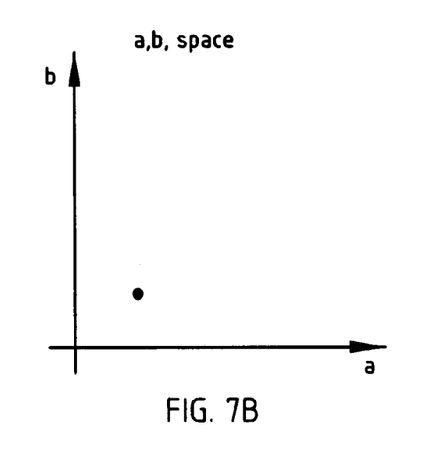
Figure 7C:
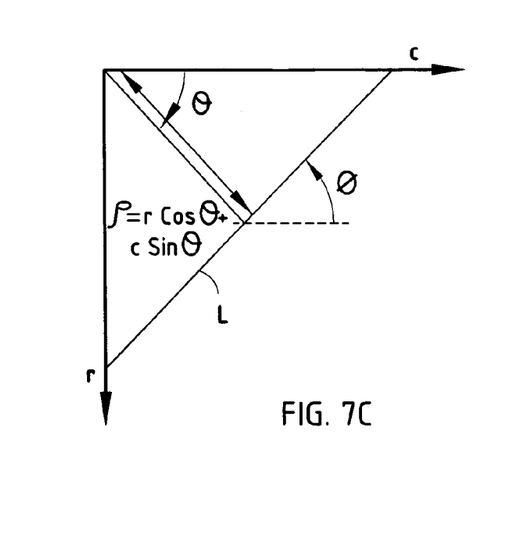

In FIG. 7A, the video image pixels that identify an edge boundary 80 of the eye 22 are plotted in a Cartesian coordinate as a function of the X- and Y-axes. By way of the Hough Transformation, the Cartesian coordinates are converted to an a, b space as seen FIG. 7B and a polar space as shown in FIG. 7C. The polar space plots lines of interest (L) as a function of r, c and $\theta$. The distance $\rho$ from a reference point is generated as a function of r, c and $\theta$ according to the following equation: $\rho = r \cos\theta + c \sin\theta$. Accordingly, a line of interest L, is defined by $\rho$ and $\theta$.

Figure 7D:
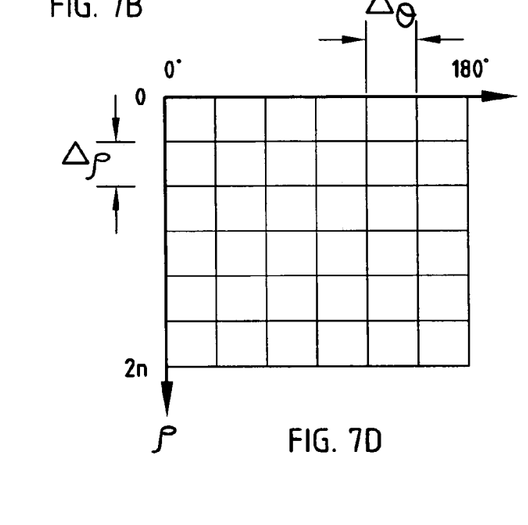

A lookup table is then created as seen in FIG. 7D. Each cell of the lookup table represents the number of edge boundary pixels of a line ($\rho$, $\theta$). $\theta$ ranges from zero degrees ($0°$) to one hundred eighty degrees ($180°$), and each cell includes a dimension size of $\Delta_\theta$. $\rho$ ranges from 0 to 2n, and has a cell dimension size of $\Delta_\rho$. Parameter n is the largest dimension of the image (i.e., width or height). The Hough Transformation provides a polar space which defines the desired increments of $\rho$ and $\theta$, $\Delta_\rho$ and $\Delta_\theta$, and quantifies this space accordingly. For every point of interest (typically points found by edge detectors that exceeds some threshold value), values for r and c are plugged into the line equation and, for each value of $\theta$ in the quantified space, the distance $\rho$ is solved for. For each $\rho$, $\theta$ pair, the rc pair in the corresponding block in the quantified space is recorded which constitutes a hit for a particular block. The number of hits in each block corresponds to the number of pixels on the line as defined by the values of $\rho$ and $\theta$ in that block. A minimum threshold is chosen as one-third of the tracking window 70 width (e.g., in the example given the width is equal to eighty-eight (88) pixels so the threshold is about twenty-nine (29) pixels) is used to select a set of lines from the lookup table.

From the Hough Transformation, representative substantially horizontal lines are chosen by extracting the coordinates of distance ρ at angle θ equals ninety degrees (θ=90°) that meet the minimum threshold requirement. The substantially horizontally lines may be chosen at angle θ=ninety degrees (90°)±X degrees, which X is an acceptable angular deviation from the horizontal position to allow for the inclusion of substantially horizontal lines. X may include seven degrees (7°), according to one embodiment. The upper and lower lines represent the upper and lower edge boundaries of the eye. The line with the minimum distance p and the line with the maximum distance p are then used to indicate the upper and lower horizontal lines 72 and 74 at the edge boundaries of the upper and lower eyelids of the eye 22, respectively.

To discriminate the eye closure states, including open eye and closed eye positions, the distance D between the upper and lower substantially horizontal lines 72 and 74 is compared to the open eye and closed eye threshold values $D_O$ and $D_C$. While the open eye and closed eye thresholds $D_O$ and $D_C$ have been shown and described herein for determining eye closure in three states, it should be appreciated that a single or other multiples of thresholds may be used depending on the desired resolution of the eye state determination.

Figure 8A:
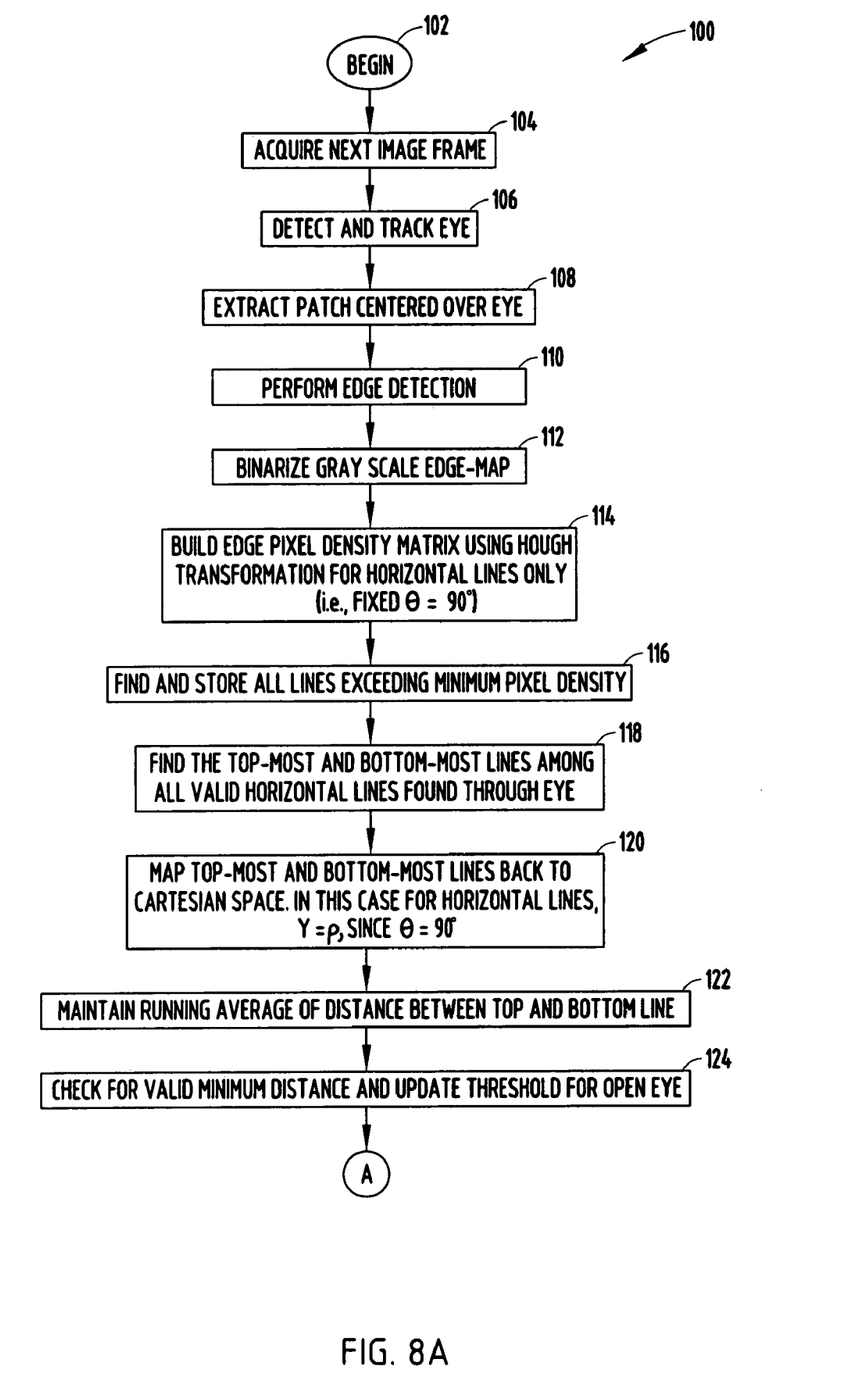
FIGS. 8A-8C is a flow diagram illustrating the eye closure recognition routine for determining the eye closure state according to the present invention.
Figure 8B:
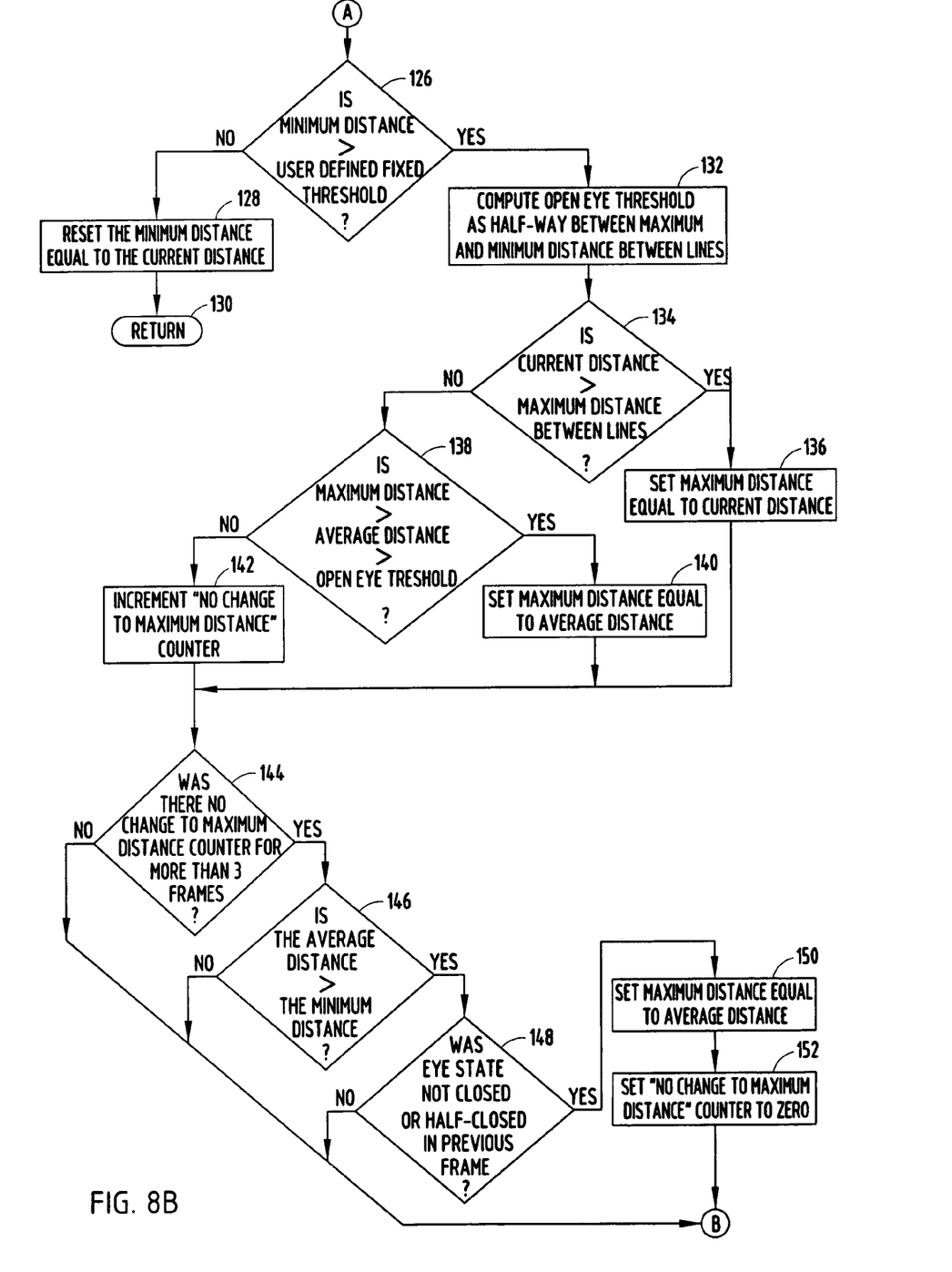
Figure 8C:
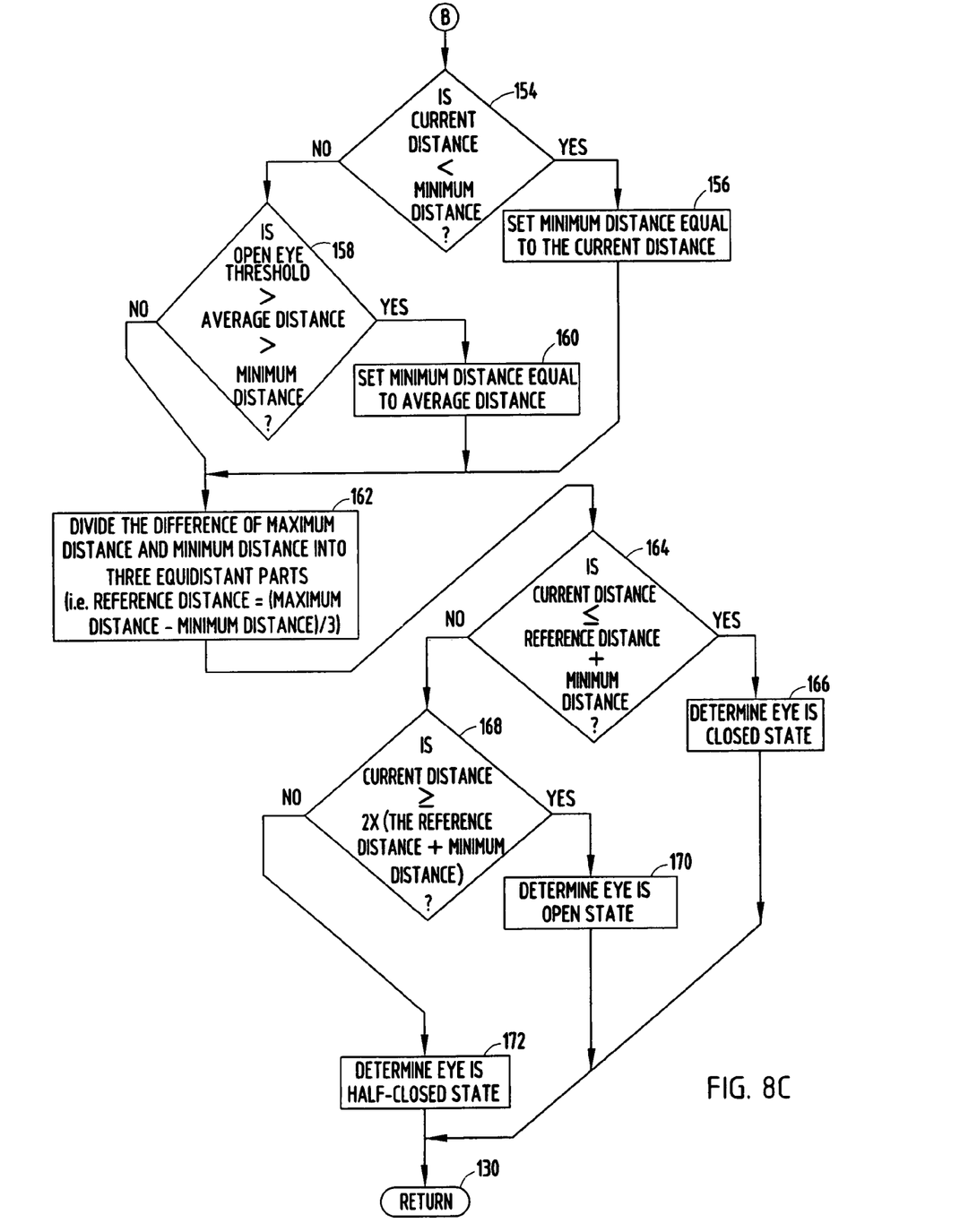

The eye closure recognition routine 100 is shown in detail in FIGS. 8A-8C. Routine 100 begins at step 102 and proceeds to step 104 to acquire the next video image frame generated by the video imaging camera. Routine 100 begins to process the acquired video image frame including detecting and tracking the subject eye in step 106. The eye detection and tracking functions may employ the use of known image pattern recognition techniques.

Proceeding to step 108, routine 100 extracts a patch as the eye tracking window centered over the subject eye. Routine 100 then performs edge detection in step 110 to determine the edge boundaries of the monitored eye, including the edges of the upper and lower eyelids. The edge detection may include the use of known edge detection software, such as a Sobel edge detector.

Eye closure recognition routine 100 binarizes a gray-scale edge-map in step 112 to provide gray-scale shading for the individual video image pixels. Certain pixels will exhibit a characteristic gray-scale image to identify the edge boundaries in the video image. Routine 100 then builds an edge pixel density matrix using the Hough Transformation and processes the substantially horizontal lines only, that is, those lines with angle θ fixed at about ninety degrees (90°) in step 114.

Proceeding to step 116, eye closure recognition routine 110 finds and stores substantially all lines exceeding a minimum pixel density. In step 118, the top-most and bottom-most among all valid substantially horizontal lines are found which extend through the eye edge boundaries. The top-most and bottom-most substantially horizontal lines are mapped back to Cartesian space in step 120. For the substantially horizontal lines, Y is set equal to ρ, since the angle θ is equal to about ninety degrees (90°).

Eye closure recognition routine 100 maintains a running average of the distance between the top (upper) and bottom (lower) substantially horizontal lines in step 122. In step 124, routine 100 checks for a valid minimum distance and updates the threshold for an open eye state. The valid minimum distance can be calibrated and saved when the eye blinks and is therefore closed. Any update to the threshold for an open eye state can be based on the minimum distance calibrated during the eye blinking (closing). By establishing the minimum distance when the eye is blinking and, thus, is expected to be closed, the eye closure threshold can be calibrated. The routine 100 adapts dynamically the values of the thresholds used to distinguish between open and closed eye states. The routine 100 may therefore perform equally for short and tall drivers as well as for the same driver at different depth levels.

Routine 100 proceeds to decision step 126 to determine if the minimum distance is greater than a user defined fixed threshold. If the minimum distance is not greater than the user defined fixed threshold, routine 100 resets the minimum distance equal to the current distance in step 128, and then returns to the beginning of the routine in step 130. If the minimum distance is greater than the user defined fixed threshold, routine 100 computes an open eye threshold as half-way between the maximum and minimum distances between the upper and lower lines in step 132.

Thereafter, routine 100 proceeds to decision step 134 to determine if the current distance D is greater than the maximum distance between the upper and lower lines and, if so, sets the maximum distance equal to the current distance in step 136. If the current distance D is not greater than the maximum distance between the lines, routine 100 proceeds to decision step 138 to determine if the average distance is less than the maximum distance and greater than the open eye threshold and, if so, sets the maximum distance equal to the average distance in step 140. If the average distance is not between the maximum distance and the open eye threshold, routine 100 proceeds to increment the "no change to maximum distance" counter in step 142.

Routine 100 then proceeds to decision step 144 to determine if there was no change to the maximum distance counter for more than three frames. If there was no change to the maximum counter for more than three frames, routine 100 proceeds to decision step 146 to determine if the average distance is greater than the minimum distance and, if so, proceeds to decision step 148.

In decision step 148, routine 100 determines if the eye state was not closed or was half-open in the previous frame and, if so, proceeds to set the maximum distance equal to the average distance of step 150, and then further proceeds to set the "no change to maximum distance" counter to zero in step 152. Following step 152 or, if the decision in each of decision steps 144, 146, and 148 is no, routine 100 proceeds to decision step 154 to determine if the current distance is less than the minimum distance. If the current distance is less than the minimum distance, routine 100 sets the minimum distance equal to the current distance in step 156. If the current distance is not less than the minimum distance, routine 100 proceeds to decision step 158 to determine if the average distance is greater than the minimum distance and less than the eye open threshold and, if so, sets the minimum distance equal to the average distance in step 160.

Following steps 156 and 160 or if the decision in step 158 is no, routine 100 proceeds to divide the difference of maximum distance and minimum distance into three equidistant parts (i.e., reference distance equals (maximum distance minus minimum distance)/3). Proceeding to decision step 164, routine 100 determines if the current distance D is less than or equal to the reference distance summed with the minimum distance and, if so, determines that the eye is in the closed state in step 166, before returning in step 130. If the current distance D is not less than or equal to the reference distance summed with the minimum distance, routine 100 proceeds to decision step 168 to determine if the current distance is greater than or equal to two times the sum of the reference distance and minimum distance and, if so, determines that the eye is in the open state in step 170, before returning in step 130. Otherwise, if the current distance D is not greater than or equal to two times the sum of the reference distance and minimum distance, routine 100 determines that the eye is in the half-closed state in step 172, before returning in step 130.

The eye closure recognition routine 100 is therefore able to discriminate whether the eye 22 is in an open state, closed state, or half-closed state based on the distance between the selected first and second lines. Further, it should be appreciated that the eye closure recognition routine 100 may determine that the eye state is closed when no boundary edges or no lines are found in the processed video frame image. Similarly, if only one line is identified, the eye closure recognition routine 100 may conclude that the eye state is closed.

The eye monitoring system 30 employs the eye closure recognition routine 100 to discriminate the closure state of a monitored subject eye 22 by comparing substantially horizontal upper and lower edge boundaries and determining an amount of eye closure based on the difference between the substantially horizontal first and second lines. The first and second lines are substantially linear and substantially parallel to each other, according to the embodiments shown and described herein. However, it is conceivable that the eye monitoring system 30 may generate non-linear lines and determine eye closure based on distance between the non-linear lines, without departing from the teachings of the present invention.

In one embodiment, the first and second lines are substantially horizontal lines that are substantially parallel to one another. It should be appreciated that the first and second lines may extend at angles slightly offset from one another, and may be at an angle other than a horizontal line relative to a ground plane according to other embodiments. It should further be appreciated that additional sensors or sensing techniques may be employed to determine an angle of head tilt, such that the eye closure recognition routine 100 may determine the eye closure state as a function of the head angle tilt by processing first and second lines that are not substantially horizontal.

Accordingly, the eye monitoring system 30 of the present invention advantageously captures and processes images of the eye 22 to determine eye closure. The eye monitoring system 30 of the present invention is economical and easy to manufacture and deploy in a vehicle. It should be appreciated that the eye monitoring system 30 may be employed in various applications employed both on and off a vehicle.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

The invention claimed is:

1. A system for monitoring an eye and determining eye closure, said system comprising:
   a video imaging camera oriented to generate images of an eye; and
   a video processor for processing the images generated with the video imaging camera, said video processor comprising an edge detector for detecting edges of the eye in the image and a line selector for generating at least first and second lines representative of the detected edges, and said processor determining a state of eye closure based on distance between the first and second lines, wherein said video processor compares the distance between the first and second lines to a threshold distance to determine if the eye is closed.

2. The system as defined in claim 1, wherein said first and second lines are substantially linear.

3. The system as defined in claim 2, wherein said first and second lines are substantially parallel to each other.

4. The system as defined in claim 3, wherein the first and second lines are substantially horizontal.

5. The system as defined in claim 1, wherein said processor dynamically determines the threshold distance when the eye is closed.

6. The system as defined in claim 1, wherein said processor performs a Hough Transformation to transform the at least first and second lines from Cartesian coordinates to polar coordinates and generates substantially parallel lines as the first and second lines.

7. The system as defined in claim 1, wherein said detected edges comprise a gray-scale representation of pixels imaging the eye.

8. The system as defined in claim 1, wherein the system is employed in a vehicle for monitoring an eye of a driver of the vehicle.

9. A vehicle eye monitoring system for monitoring an eye of a-person in a vehicle and determining eye closure, said system comprising:
   a video imaging camera located on a vehicle and oriented to generate images of an eye of a person in the vehicle; and
   a processor for processing the images generated with the video imaging camera, said video processor comprising an edge detector for detecting edges of the eye in the image and a line selector for generating first and second lines representative of the detected edges, said processor determining a state of eye closure based on distance between the first and second lines, wherein said processor compares the distance between the first and second lines to a threshold distance to determine if the eye is closed.

10. The system as defined in claim 1, wherein said first and second lines are substantially linear and substantially parallel to each other.

11. The system as defined in claim 10, wherein said first and second lines are substantially horizontal.

12. The system as defined in claim 9, wherein said processor dynamically determines the threshold distance when the eye is closed.

13. The system as defined in claim 9, wherein said line selector comprises a Hough Transformation for transforming the at least first and second lines from Cartesian coordinates to polar coordinates and generates substantially parallel lines as the first and second lines.

14. A method of monitoring an eye and determining eye closure, said method comprising the steps of:
   arranging a video imaging camera to generate images of an eye;
   generating an image of the eye;
   processing the image to identify edges of the eye in the image;
   generating at least first and second lines representative of the edges; and
   determining an eye closure state based on distance between the first and second lines, wherein said step of determining an eve closure state comprises comparing the distance between the first and second lines to a threshold distance to determine if the eye is closed.

15. The method as defined in claim 14, wherein the step of generating at least first and second lines comprises generating first and second lines that are substantially linear and substantially parallel to each other.

16. The method as defined in claim 15, wherein the step of generating at least first and second lines comprises generating first and second lines that are substantially horizontal.

17. The method as defined in claim 14 further comprising the step of dynamically determining the threshold distance when the eye is closed.

18. The method as defined in claim 14, wherein the step of generating at least first and second lines comprises transforming first and second lines from Cartesian coordinates to polar coordinates with a Hough Transformation to generate substantially parallel lines as the first and second lines.

19. The method as defined in claim 14, wherein said step of arranging a video camera comprises arranging the video camera in a vehicle to monitor the eye of the driver of the vehicle.

* * * * *